US012318270B2

(12) United States Patent
Gong et al.

(10) Patent No.: US 12,318,270 B2
(45) Date of Patent: Jun. 3, 2025

(54) ABSORBENT ARTICLE

(71) Applicant: Kimberly-Clark Worldwide, Inc., Neenah, WI (US)

(72) Inventors: Pei Gong, Shanghai (CN); Lin Miao, Beijing (CN); Qiaoping Li, Shanghai (CN)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 567 days.

(21) Appl. No.: 17/594,427

(22) PCT Filed: Apr. 17, 2019

(86) PCT No.: PCT/CN2019/082992
§ 371 (c)(1),
(2) Date: Oct. 15, 2021

(87) PCT Pub. No.: WO2020/210999
PCT Pub. Date: Oct. 22, 2020

(65) Prior Publication Data
US 2022/0096281 A1    Mar. 31, 2022

(51) Int. Cl.
*A61F 13/49* (2006.01)

(52) U.S. Cl.
CPC .... *A61F 13/49017* (2013.01); *A61F 13/4902* (2013.01); *A61F 2013/49025* (2013.01); *A61F 2013/49092* (2013.01)

(58) Field of Classification Search
CPC ................ A61F 13/49; A61F 13/49017; A61F 13/4902; A61F 13/4906; A61F 13/49446;
(Continued)

(56) References Cited

U.S. PATENT DOCUMENTS

| 4,657,539 A | 4/1987 | Hasse |
| 5,032,120 A | 7/1991 | Freeland et al. |

(Continued)

FOREIGN PATENT DOCUMENTS

| CN | 1192888 A | 9/1998 |
| CN | 1744870 A | 3/2006 |

(Continued)

OTHER PUBLICATIONS

Tyemedical "LivDry Premium Briefs", Tyemedical.com, https://www.tyemedical.com/product/livdry-premium-briefs/.
(Continued)

*Primary Examiner* — Catharine L Anderson
*Assistant Examiner* — Lynne Anderson
(74) *Attorney, Agent, or Firm* — KIMBERLY-CLARK WORLDWIDE, INC.

(57) ABSTRACT

An absorbent article (10) has a front region (20), a back region (30), and a crotch region (40) extending between and connecting the front region (20) and the back region (30). The absorbent article (10) can have non-linear leg edges (82, 84) extending between and connecting the front region (20) and the back region (30). The absorbent article (10) can have an absorbent article (10) narrowest width (80) positioned between the waist edge (22) of the front region (20) and the transverse axis (14) of the absorbent article (10). A non-linear leg elastic (140) can extend from one side edge (34) of the back region (30) to another side edge (36) of the back region (30) and can have an apex (142) located between the absorbent article (10) narrowest width (80) and the transverse axis (14).

16 Claims, 7 Drawing Sheets

(58) Field of Classification Search
CPC ...... A61F 13/49453; A61F 2013/15365; A61F 2013/49025; A61F 2013/49068; A61F 2013/49074; A61F 2013/49076; A61F 2013/49082; A61F 2013/4909; A61F 2013/49092

See application file for complete search history.

(56) References Cited

U.S. PATENT DOCUMENTS

| | | | |
|---|---|---|---|
| 5,085,654 | A | 2/1992 | Buell |
| 5,204,997 | A | 4/1993 | Suzuki et al. |
| 6,375,646 | B1 | 4/2002 | Widlund et al. |
| 6,443,933 | B1 | 9/2002 | Suzuki et al. |
| 6,500,161 | B1 | 12/2002 | Freiburger et al. |
| 6,726,669 | B2 | 4/2004 | Shimada et al. |
| 7,172,669 | B2 | 2/2007 | Norrby |
| 7,331,946 | B2 | 2/2008 | Shimada et al. |
| 7,699,827 | B2 | 4/2010 | Sandin et al. |
| 7,959,618 | B2 | 6/2011 | Hermansson et al. |
| 8,016,805 | B2 * | 9/2011 | Sasaki ............... A61F 13/15203 604/385.24 |
| 8,057,455 | B2 | 11/2011 | Shirai et al. |
| 8,083,724 | B2 * | 12/2011 | Bittner ............... A61F 13/49019 604/385.24 |
| 8,206,365 | B2 | 6/2012 | Norrby |
| 8,303,562 | B2 | 11/2012 | Hornung et al. |
| 8,449,515 | B2 * | 5/2013 | Saito ................. A61F 13/49017 604/385.27 |
| 8,518,010 | B2 | 8/2013 | Kuwano et al. |
| 8,523,835 | B2 | 9/2013 | Malowaniec |
| 8,647,319 | B2 * | 2/2014 | Een ................... A61F 13/49011 604/385.27 |
| 8,915,900 | B2 | 12/2014 | Shimada et al. |
| 8,939,956 | B2 | 1/2015 | Mukai et al. |
| 9,265,669 | B2 | 2/2016 | Bennett et al. |
| 9,283,125 | B2 | 3/2016 | Otsubo et al. |
| 9,320,658 | B2 | 4/2016 | Arayama et al. |
| 9,333,120 | B2 | 5/2016 | Lavon et al. |
| 9,956,124 | B2 | 5/2018 | Back et al. |
| 10,034,801 | B2 | 7/2018 | Seitz et al. |
| 10,092,457 | B2 | 10/2018 | Ishikawa et al. |
| 2002/0049421 | A1 | 4/2002 | Hayase et al. |
| 2005/0080394 | A1 | 4/2005 | Otsubo et al. |
| 2005/0107763 | A1 | 5/2005 | Matsuda et al. |
| 2006/0025746 | A1 | 2/2006 | Sasaki et al. |
| 2008/0249491 | A1 | 10/2008 | Young et al. |
| 2009/0275911 | A1 | 11/2009 | Hornung et al. |
| 2011/0209270 | A1 | 9/2011 | Carlson et al. |
| 2013/0197463 | A1 * | 8/2013 | Malowaniec ....... A61F 13/5644 604/386 |
| 2015/0065982 | A1 | 3/2015 | Hamilton et al. |
| 2016/0100997 | A1 | 4/2016 | Seitz et al. |
| 2018/0214319 | A1 | 8/2018 | Inoue et al. |

FOREIGN PATENT DOCUMENTS

| | | |
|---|---|---|
| CN | 101222893 A | 7/2008 |
| CN | 101287432 A | 10/2008 |
| CN | 101868212 A | 10/2010 |
| CN | 102014821 A | 4/2011 |
| CN | 106029023 A | 10/2016 |
| CN | 106102676 A | 11/2016 |
| CN | 106999315 A | 8/2017 |
| CN | 108135756 A | 6/2018 |
| CN | 109069314 A | 12/2018 |
| WO | 9418927 A1 | 9/1994 |
| WO | 2004078084 A1 | 9/2004 |
| WO | 2016104184 A1 | 6/2016 |

OTHER PUBLICATIONS

TENA, "TENA Flex Maxi One Piece Belted Brief for Moderate to Heavy Incontinence Protection", Incontinence products plus.com, https://www.incontinenceproductsplus.com/TENA-Flex-Maxi-One-Piece-Belted-Brief-p/55543a.htm.

Invacare, "Incontinence & Urological Products—Adult Briefs & Protective Underwear", Invacare Supply Group, https://smhttp-ssl-51929.nexcesscdn.net/media/attachment/file/i/n/incontinence_urological_ws.pdf.

* cited by examiner

ABSORBENT ARTICLE

BACKGROUND OF THE DISCLOSURE

Child care, feminine care, and adult hygiene-related absorbent personal care articles are often used to protect a wearer's outer garments from soiling, and to collect and retain body exudates such as menses, blood, feces, and urine. Such articles are often presented in disposable garment-like product formats (as opposed to inserts, pads, or liners) and are worn as undergarments in the place of traditional underwear. They are most commonly placed on a wearer by being pulled up about a wearer's legs towards the wearer's lower abdomen and placed adjacent a wearer's crotch region during use.

Today, many wearers of absorbent garment-like articles include adults who experience various forms of incontinence. Primary desired attributes of such garments include the garment retaining body exudate, minimal or no leakage of body exudate, close-to-body fit of the garment, and that it resembles traditional woven underwear. Consumers are interested in such attributes as there is a desire to enhance the overall personal experience of using such products while reducing incontinence-related stigma. Consumers want a garment that will meet their needs without signaling to others that they are wearing such absorbent garment-like articles. Absorbent article stigmas are aggravated by product designs which can feel bulky, may gap away from the wearer's body producing an outline that can be seen through a wearer's clothing, may be manufactured from materials that can create relatively high levels of noise during use due to the specific product construction materials, and by an overall artificial visual appearance of such products when viewed by the wearer and also by third parties.

In order to improve the fit of garment-like articles, many garment-like articles are formed by positioning an absorbent assembly between or otherwise bonded to at least one stretchable or elastomeric outer layer of the garment-like article. The stretchable or elastomeric outer layer can extend transversely and longitudinally beyond the dimensional boundaries of the absorbent assembly such as into the waist region of the garment or into areas that would contact a wearer's hips when the garment is worn. Many such garments, however, do not provide the level of comfortable discretion that is desired by consumers. The material forming the garments may be shaped in such a way as to chafe against the skin of the wearer during use of the garment. The interaction between the stretchable materials and the absorbent material can cause protrusion of the absorbent material away from the wearer's body. Garments with active elastic materials positioned over and around the absorbent material can cause the absorbent material to bunch up and protrude away from the wearer's body while garments without active elastic materials over and around the absorbent material can fail to hold the absorbent material tight against the wearer's body also resulting in protrusion of the absorbent material away from the wearer's body. Crotch elastic materials which are positioned too far from the absorbent material can result in the crotch region of the garment sagging away from the body of the wearer due to the weight of the absorbent material particularly after insult by body exudate. This combination of ill-fitting garment elements results in garment distortion which can lead to discomfort, irritation, and indiscretion. Such ill-fitting garments can also increase the incidence of body exudate leakage from the garment.

There is a need for an absorbent article having an improved fit about the lower torso of the wearer. Such is desirable so as to provide a more comfortable fit across different areas of a wearer's anatomy.

SUMMARY OF THE DISCLOSURE

An absorbent article can have a longitudinal direction and a transverse direction; a longitudinal axis and a transverse axis; a front region comprising a first waist edge, a first longitudinal direction side edge, a second longitudinal direction side edge transversely opposed to the first longitudinal direction side edge; a back region comprising a second waist edge, a third longitudinal direction side edge, a fourth longitudinal direction side edge transversely opposed to the third longitudinal direction side edge; a crotch region located between the front region and the back region and comprising an absorbent article narrowest width in the transverse direction wherein the absorbent article narrowest width is located between the transverse axis and the first waist edge; an absorbent article length measured from the first waist edge to the second waist edge; a first non-linear leg edge extending between and connecting the first longitudinal direction side edge of the front region to the third longitudinal direction side edge of the back region; a second non-linear leg edge extending between and connecting the second longitudinal direction side edge of the front region to the fourth longitudinal direction side edge of the back region; a first configuration wherein, in an unfolded and laid-flat configuration, the first longitudinal direction side edge of the front region is aligned with the third longitudinal direction side edge of the back region and a first longitudinal direction plane is formed between the first longitudinal direction side edge and the third longitudinal direction side edge; a first transverse direction distance measured from a first position on the first longitudinal direction plane to a first position on the first non-linear leg edge located at the absorbent article narrowest width; a second transverse direction distance measured from a second position on the first longitudinal direction plane located at one-quarter of the absorbent article length from the first waist edge to a second position on the first non-linear leg edge wherein the second transverse direction distance is greater than 75% of the first transverse direction distance; and a first non-linear leg elastic extending from the third longitudinal direction side edge of the back region to the fourth longitudinal direction side edge of the back region and having an apex positioned between the absorbent article narrowest width and the transverse axis.

In various embodiments, the absorbent article can further have a third transverse direction distance measured from a third position on the first longitudinal direction plane located at five-eighths of the absorbent article length from the first waist edge to a third position on the first non-linear edge wherein the third transverse direction distance is less than 70% of the first transverse direction distance.

In various embodiments, the absorbent article can further have a second configuration wherein a first side seam is formed by bonding the first longitudinal direction side edge of the front region to the third longitudinal direction side edge of the back region and a second side seam is formed by bonding the second longitudinal direction side edge of the front region to the fourth longitudinal direction side edge of the back region.

In various embodiments, a tangent line to the first non-linear leg edge is not parallel to the transverse axis of the absorbent article along the entire length of the first non-linear leg edge.

In various embodiments, the second transverse direction distance is greater than 80% of the first transverse direction distance.

In various embodiments, the third transverse direction distance is less than 65% of the first transverse direction distance.

In various embodiments, the absorbent article can further have a chassis wherein the chassis comprises a first nonwoven layer and a second nonwoven layer. In various embodiments, the first nonwoven layer of the chassis and the second nonwoven layer of the chassis extend continuously from the first waist edge of the absorbent article to the second waist edge of the absorbent article. In various embodiments, a first elastic material can be sandwiched between the first nonwoven layer and the second nonwoven layer in the front region and extending in the transverse direction from the first longitudinal direction side edge to the second longitudinal direction side edge in the front region and a second elastic material can be sandwiched between the first nonwoven layer and the second nonwoven layer in the back region and extending in the transverse direction from the third longitudinal direction side edge to the fourth longitudinal direction side edge in the back region. In various embodiments, the first elastic material and the second elastic material is a plurality of elastomeric strands. In various embodiments, the first elastic material and the second elastic material is an elastomeric polymeric film layer.

In various embodiments, the absorbent article can further have an absorbent assembly bonded to the first nonwoven layer of the chassis, the absorbent assembly comprising a topsheet layer, a backsheet layer, and an absorbent core positioned between the topsheet layer and the backsheet layer. In various embodiments, the absorbent assembly can have a first longitudinally extending containment flap and a second longitudinally extending containment flap transversely opposed to the first longitudinally extending containment flap. In various embodiments, each of the first longitudinally extending containment flap and the second longitudinally extending containment flap comprise a portion positioned between the backsheet layer of the absorbent assembly and the first nonwoven layer of the chassis.

In various embodiments, each of the first longitudinal direction side edge and the second longitudinal direction side edge have a longitudinal length less than 25% of the absorbent article length. In various embodiments, each of the third longitudinal direction side edge and the fourth longitudinal direction side edge have a longitudinal length less than 25% of the absorbent article length.

Figure 1:
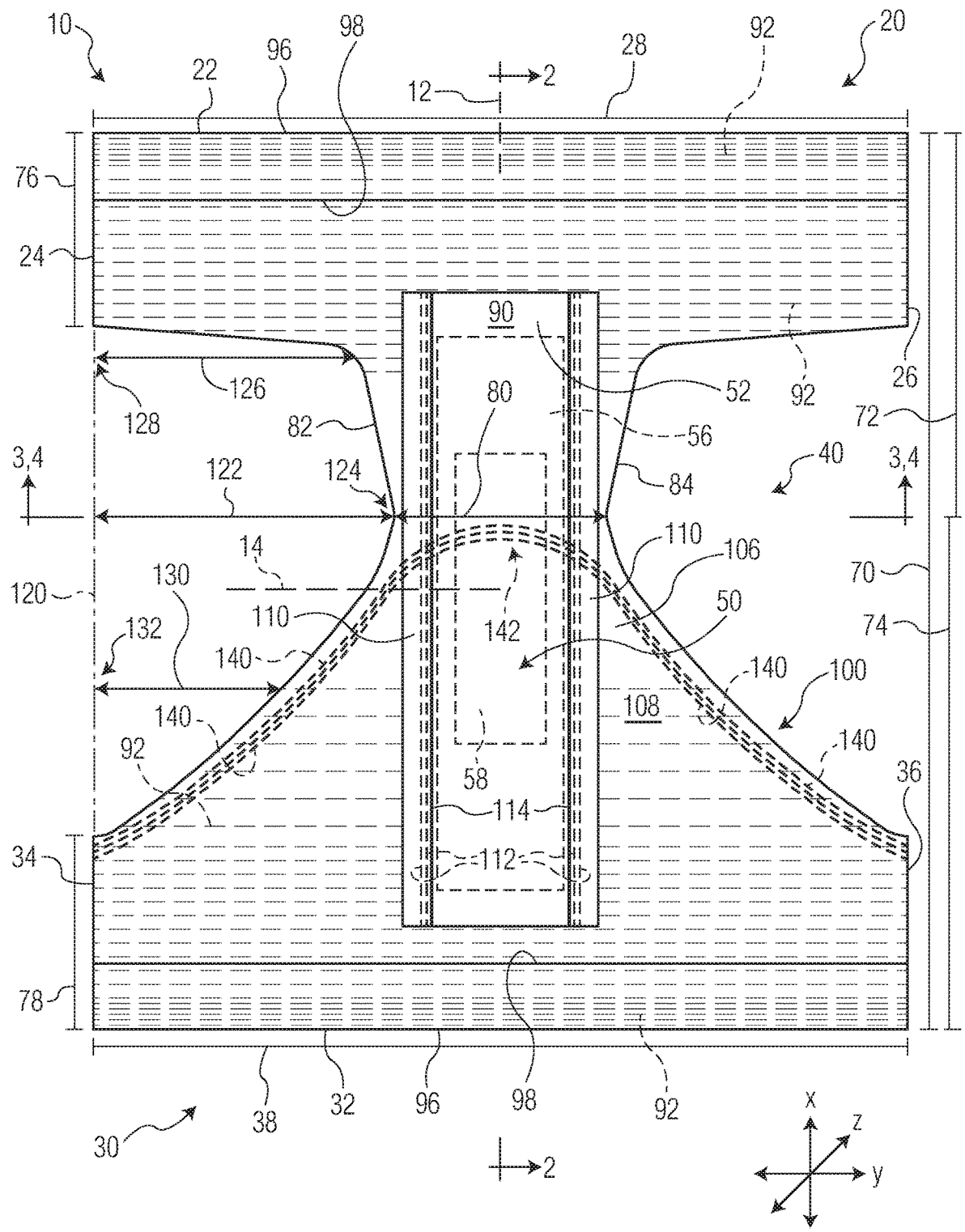
FIG. 1 is an illustration of a plan view of an embodiment of an absorbent article in a first configuration which is a longitudinally and transversely stretched and laid-flat configuration with the surface of the absorbent article that faces the wearer when the absorbent article is worn facing the viewer.

Repeat use of reference characters in the present specification and drawings is intended to represent the same or analogous features or elements of the disclosure.

DETAILED DESCRIPTION OF THE DISCLOSURE

An absorbent article has a front region, a back region, and a crotch region extending between and connecting the front region and the back region. The absorbent article can have non-linear leg edges extending between and connecting the front region and the back region. The absorbent article can have an absorbent article narrowest width positioned between the waist edge of the front region and the transverse axis of the absorbent article. A non-linear leg elastic can extend from one side edge of the back region to another side edge of the back region and can have an apex located between the absorbent article narrowest width and the transverse axis.

As used herein, the term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, enuresis garments, menstrual pants, and adult incontinence garments, and the like without departing from the scope of the present disclosure.

As used herein, the term "airlaid" refers herein to a web manufactured by an airlaying process In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form on fiber. Conjugate fibers are also sometimes referred to as bicomponent or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al., each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter.

Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Buten, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10, or 20 gsm to about 120,125, or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent," or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in par on iconicity (a factor of the ionic concentration of the aqueous solution), and the SAP functional polar groups that have an affinity for water. SAP are typically made from the polymerization of acrylic acid blended with sodium hydroxide 1 the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating or another material or fiber.

Figure 2:
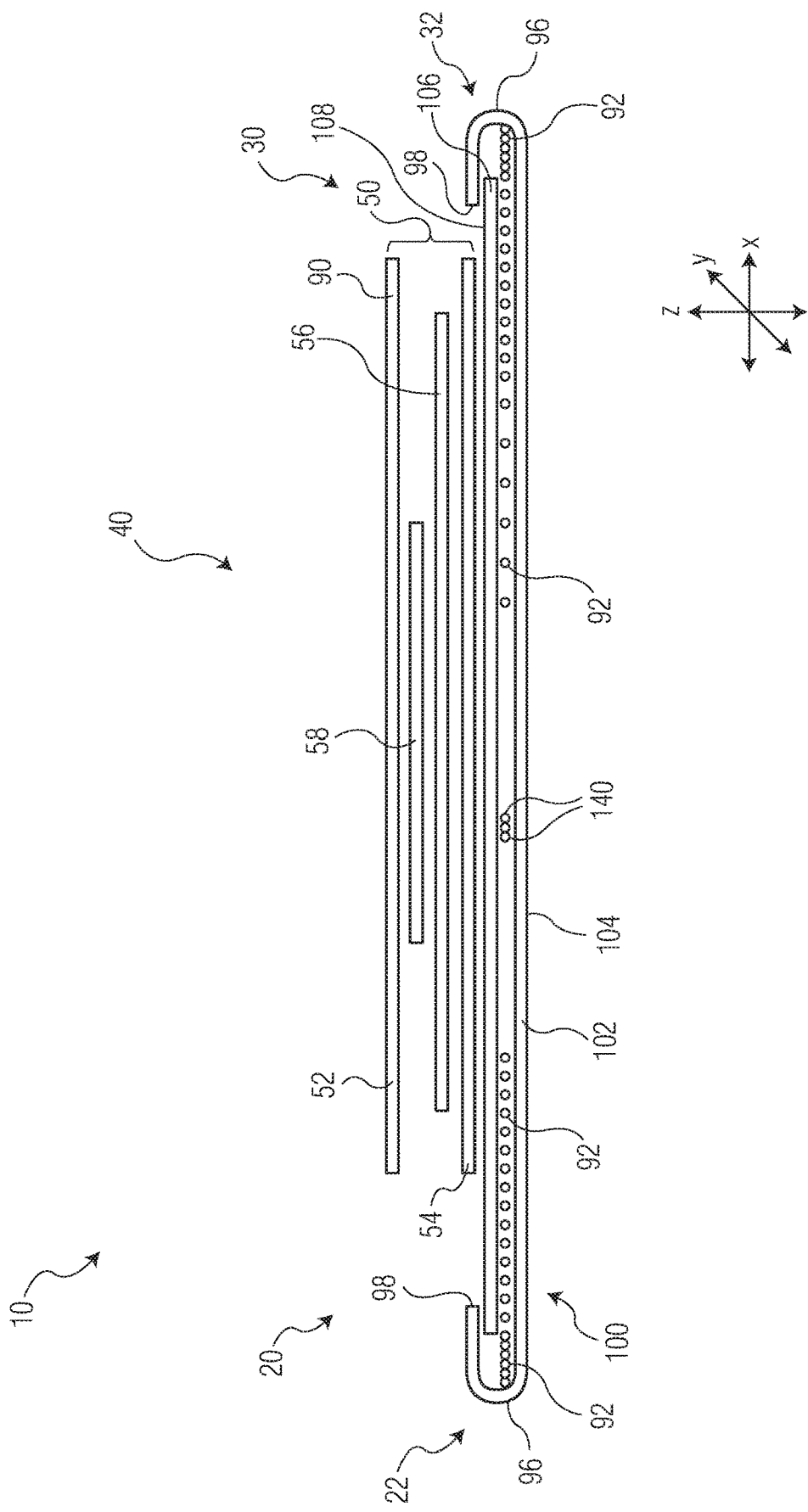
FIG. 2 is an illustration of a cross-sectional view of an embodiment of the absorbent article of FIG. 1 taken along line 2-2.
Figure 3:
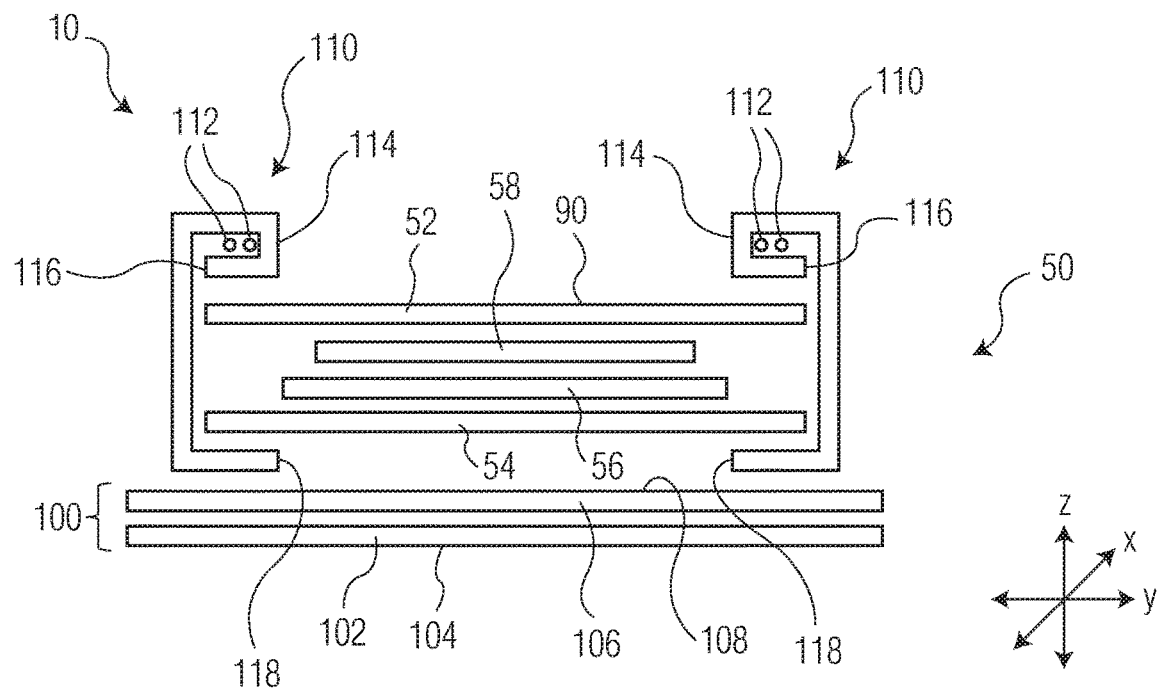
FIG. 3 is an illustration of an embodiment of a cross-sectional view of the absorbent article of FIG. 1 taken along line 3-3.
Figure 4:
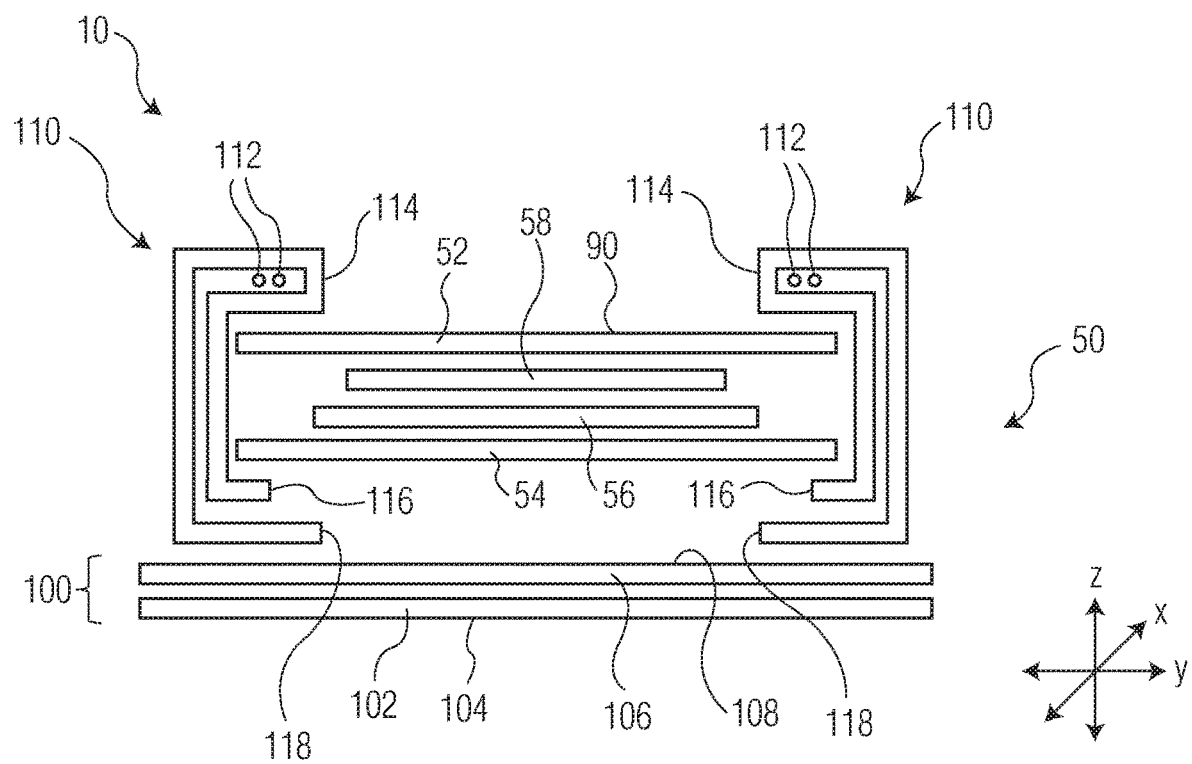
FIG. 4 is an illustration of another embodiment of a cross-sectional view of the absorbent article of FIG. 1 taken along line 4-4.

Referring to FIGS. 1-4, an illustration of an exemplary embodiment of an absorbent article 10 is illustrated. FIG. 1 provides an illustration of a plan view of an embodiment of an absorbent article 10 in a first configuration which is an unfolded, longitudinally and transversely stretched and laid-flat configuration with the surface of the absorbent article 10 that faces the wearer when the absorbent article 10 is worn facing the viewer, FIG. 2 provides an illustration of a cross-sectional view of an embodiment of the absorbent article 10 of FIG. 1 taken along line 2-2, FIG. 3 provides an illustration of a cross-sectional view of an embodiment of the absorbent article 10 of FIG. 1 taken along line 3-3, and FIG. 4 provides an illustration of a cross-sectional view of another embodiment of the absorbent article 10 of FIG. 1 taken along line 4-4. Although for illustrative purposes certain features of the present disclosure can be described and illustrated with respect to an adult incontinence garment, the various aspects and embodiments of the present disclosure are also suitable for use with diapers, youth pants, swim pants, training pants, enuresis garments, menstrual pants, and the like.

The absorbent article 10 has a longitudinal direction (X), a transverse direction (Y), and a depth direction (Z). The absorbent article 10 can have a longitudinal axis 12 and a transverse axis 14. The absorbent article 10 is intended to be worn about the lower torso of a human and can have a front region 20, a back region 30, and a crotch region 40 extending between and connecting the front region 20 and the back region 30. The front region 20 and the back region 30 are those regions of the absorbent article 10 that are fitted circumferentially around at least the lower torso of the wearer of the absorbent article 10 including, for example, the wearers abdomen, lower back, buttock, and hips. The crotch region 40 of the absorbent article 10 is that region of the absorbent article 10 that will be positioned between the wearer's legs when the absorbent article 10 is fitted onto the wearer.

Figure 7:
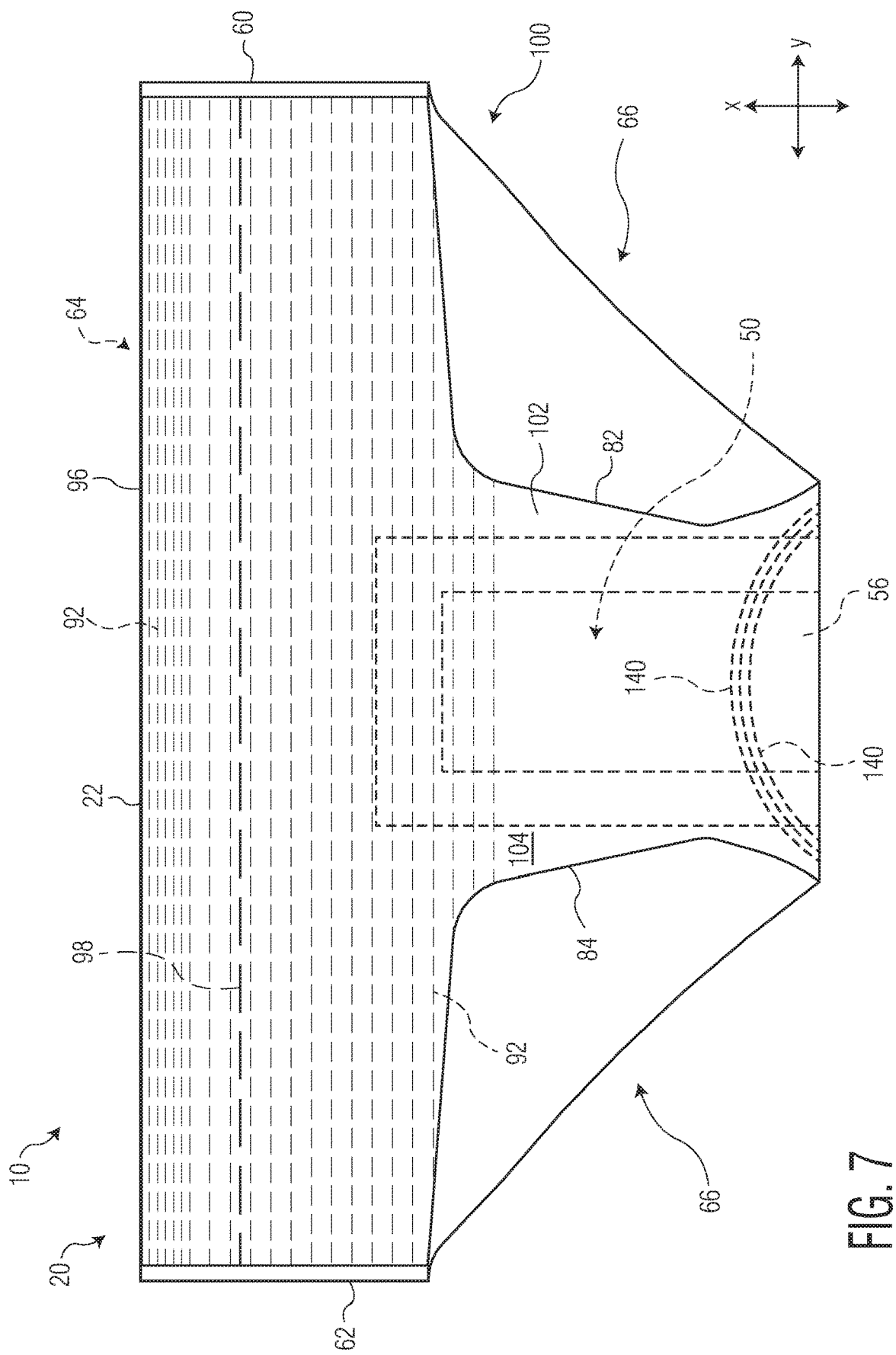
FIG. 7 is an illustration of a front view of an embodiment of the absorbent article of FIG. 1 in a second configuration which is a pull-on, pant-like configuration.
Figure 8:
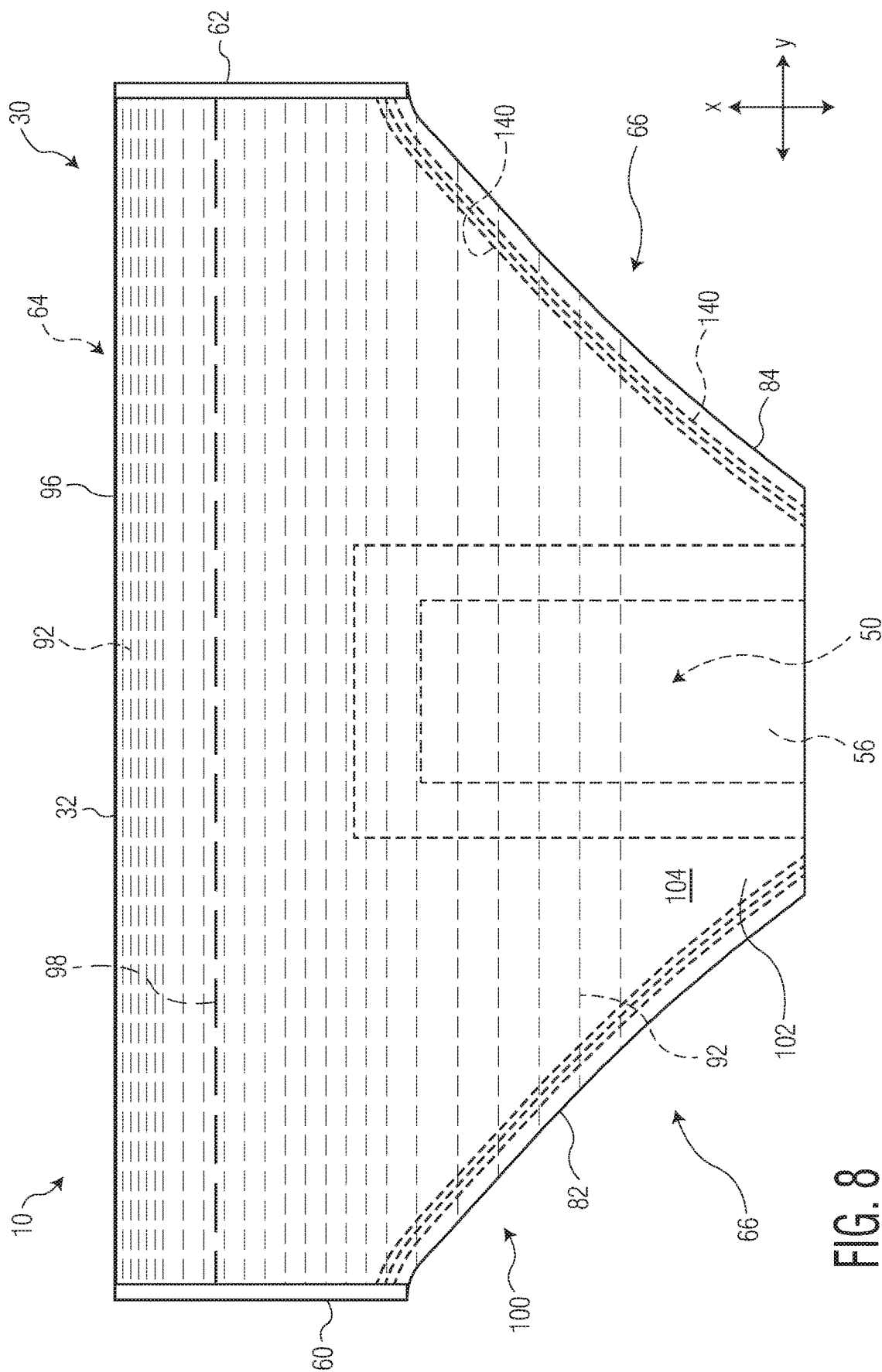
FIG. 8 is an illustration of a back view of the absorbent article of FIG. 7.

In the first configuration, which is an unfolded, stretched, and laid-flat configuration such as, for example, illustrated in FIG. 1, the front region 20 has a front waist edge 22, a first longitudinal direction side edge 24, and a second longitudinal direction side edge 26 transversely opposed to the first longitudinal direction side edge 24. The back region 30 has a back waist edge 32, a first longitudinal direction side edge 34, and a second longitudinal direction side edge 36 transversely opposed to the first longitudinal direction side edge 34. To place the absorbent article 10 into a second configuration which is a suitable configuration for wearing about the lower torso of the wearer, such as, for example, illustrated in FIGS. 7 and 8, the first longitudinal direction side edge 24 of the front region 20 can be bonded to the first longitudinal direction side edge 34 of the back region 30 to form a first side seam 60 and the second longitudinal direction side edge 26 of the front region 20 can be bonded to the second longitudinal direction side edge 36 of the back region 30 to form a second side seam 62. Forming the side seams, 60 and 62, can create a wearable absorbent article 10 having a waist opening 64 and a pair of leg openings 66 such as, for example, illustrated in FIGS. 7 and 8.

The front region 20 can have a front region width 28 measured in the transverse direction (Y) between the first longitudinal direction side edge 24 and the second longitudinal direction side edge 26. The front region width 28 is measured with the absorbent article 10 fully extended in the transverse direction (Y) such as illustrated in FIG. 1 when the absorbent article 10 is in the first configuration and is in a longitudinally and transversely stretched and laid-flat configuration prior to the joining of the front and back regions, 20 and 30, respectively, to form the side seams, 60 and 62, of the second configuration of the absorbent article 10. As used herein, the term "fully extended" describes the condition wherein the absorbent article 10 is extended in a given direction to the point where any further extension in said direction would result in one or more material failures (e.g., rupture or permanent deformation). In various embodiments, the front region width 28 may be from 520 or 540 mm to 850 or 900 mm.

The back region 30 can have a back region width 38 measured in the transverse direction (Y) between the first longitudinal direction side edge 34 and the second longitudinal direction side edge 36 of the back region 30. The back region width 38 is measured with the absorbent article 10 fully extended in the transverse direction (Y) such as illustrated in FIG. 1 when the absorbent article 10 is in a first configuration and is in a longitudinally and transversely stretched and laid-flat configuration prior to the joining of the front and back regions, 20 and 30, respectively, to form the side seams, 60 and 62, of the second configuration of the absorbent article 10. In various embodiments, the back region width 38 may be from 520 or 540 mm to 850 or 900 mm.

The absorbent article 10 has an absorbent article length 70 as measured in the longitudinal direction (X) from the front waist edge 22 to the back waist edge 32 as illustrated in FIG. 1. The absorbent article length 70 is measured with the absorbent article 10 fully extended in the longitudinal direction (X) such as illustrated in FIG. 1 when the absorbent article 10 is the first configuration and is in a longitudinally and transversely stretched and laid-flat configuration prior to the joining of the front and back regions to form the side seams, 60 and 62, of the second configuration of the absorbent article 10. In various embodiments, the absorbent article length 70 may be at least 530, 560, 600, 620, 640, 660, 680, 700, 720, 740, 760, 780, 800, or 820 mm. The first longitudinal direction side edge 24 and the second longitudinal direction side edge 26 of the front region 20 can each have a length 76 measured in the longitudinal direction (X) of the absorbent article 10 which is less than 25% of the absorbent article length 70. The first longitudinal direction side edge 34 and the second longitudinal direction side edge 36 of the back region 30 can each have a length 78 measured in the longitudinal direction (X) of the absorbent article 10 which is less than 25% of the absorbent article length 70.

The crotch region 40 is disposed in the longitudinal direction (X) between and interconnecting the front region 20 and the back region 30. The absorbent article has an absorbent article narrowest width 80 located within the crotch region 40 of the absorbent article 10. The absorbent article narrowest width 80 is measured in the transverse direction (Y) as the narrowest dimension between a first non-linear leg edge 82 and a second non-linear leg edge 84 such as illustrated in FIG. 1. Each of the leg edges, 82 and 84, are non-linear such that a tangent line to each of the leg edges, 82 and 84, is not parallel to the transverse axis 14 of the absorbent article 10 along the entire length of the non-linear leg edges, 82 and 84. The absorbent article narrowest width 80 is measured with the absorbent article 10 in the first configuration and in a longitudinally and transversely stretched and laid-flat configuration prior to the joining of the front and back regions to form the side seams, 60 and 62, of the second configuration of the absorbent article 10. In various embodiments, the absorbent article narrowest width 80 is less than 30%, 25% or 20% of the front region width 28. For example, in various embodiments, the absorbent article narrowest width 80 may be about 150 mm and the front region width 28 may be about 630 mm or 740 mm. In such embodiments, the absorbent article narrowest width 80 may be about 24% or 20% of the front region width 28, respectively. As another example, in various embodiments, the absorbent article narrowest width 80 may be about 150 mm and the front region width 80 may be about 750 mm or 880 mm. In such embodiments, the absorbent article narrowest width 80 may be about 20% or 17% of the front region width 28, respectively. The lower the percentage of the absorbent article narrowest width 80, relative to the front region width 28, the more shaped the absorbent article 10 is within the crotch region 40. In other words, the higher the percentage (up to 100%) the more rectangular the absorbent article 10 is within the crotch region 40. An absorbent article 10 having a more rectangular shape within the crotch region 40 may provide too much bulk of an absorbent article 10 between the wearer's legs which fails to follow the contours of the wearer's legs. This can result in the absorbent article 10 bunching up between the wearer's legs, protruding away from the body of the wearer, and not fitting close to the body of the wearer at the location where body exudate exits the body of the wearer. Providing a non-rectangular shape to the absorbent article 10 within the crotch region 40 of the absorbent article 10 can remove bulk from between the wearer's legs and allow the absorbent article 10 to better fit against and between the contours of the wearer's legs. This can allow for improved conformance of the absorbent article 10 to the body of the wearer.

In various embodiments, the absorbent article narrowest width 80 is positioned between the front waist edge 22 and the transverse axis 14 of the absorbent article 10. In such embodiments, the absorbent article narrowest width 80 is not in an overlapping alignment with the transverse axis 14 of the absorbent article 10. The absorbent article narrowest width 80 can apportion the absorbent article length 70 into a first article sub-length 72 and a second article sub-length 74. The first article sub-length 72 can be measured in the longitudinal direction (X) from the front waist edge 22 to the absorbent article narrowest width 80 when the absorbent article 10 is in a longitudinally and transversely stretched and laid-flat configuration prior to the joining of the front and back regions to form the side seams, 60 and 62. The second article sub-length 74 can be measured in the longitudinal direction (X) from the back waist edge 32 to the absorbent article narrowest width 80 when the absorbent article 10 is in a longitudinally and transversely stretched and laid-flat configuration prior to the joining of the front and back regions to form the side seams, 60 and 62. In various embodiments, the first article sub-length 72 is less than the second article sub-length 74. In various embodiments, the first article sub-length 72 can be less than 45% or 40% of the total article length 70. In various embodiments, the second article sub-length 74 can be greater than 55% or 60% of the total article length 70. Wearers of absorbent articles 10 have body shapes in a variety of shapes, sizes, and curvature, and are generally not symmetrical. Placing an absorbent article 10 that is symmetrical about the transverse axis 14 on a body which is not symmetrical can result in a reduction in proper fit of the absorbent article 10 on the body of the wearer. Positioning the absorbent article narrowest width 80 closer to the front waist edge 22, and not in alignment with the transverse axis 14, can provide for a non-symmetrical about the transverse axis 14 absorbent article 10. As a result, when the absorbent article narrowest width 80 is positioned between the legs of the wearer a greater proportion of the absorbent article 10 is positioned on the posterior side of the wearer's body providing for better coverage of the buttocks of the wearer of the absorbent article 10.

When the absorbent article 10 is in the first configuration such that the absorbent article 10 is in a longitudinally and transversely stretched and laid-flat configuration, the first longitudinal direction side edge 24 of the front region 20 can be aligned with the first longitudinal direction side edge 34 of the back region 30 such that a longitudinal direction plane 120 is formed between the first longitudinal direction side edge 24 of the front region 20 and the first longitudinal direction side edge 34 of the back region 30. In such a configuration, a first transverse direction distance 122 can be measured in the transverse direction (Y) from the longitudinal direction plane 120 to a first position 124 on the first non-linear leg edge 82 wherein the first position 124 on the first non-linear leg edge 82 is located at the absorbent article narrowest width 80. In various embodiments, the first transverse direction distance 122 can be the largest transverse direction distance between the longitudinal direction plane 120 and the first non-linear leg edge 82. A second transverse direction distance 126 can be measured in the transverse direction (Y) from the longitudinal direction plane 120 to the first non-linear leg edge 82. The starting point of the second transverse direction distance 126 can be a position 128 on the longitudinal direction plane 120 located at a distance from the first waist edge 22 which is one-quarter of the absorbent article length 70. The second transvers direction distance 126 can be greater than 75% or 80% of the first transverse direction distance 122. A third transverse direction distance 130 can be measured in the transverse direction (Y) from the longitudinal direction plane 120 to the first non-linear leg edge 82. The starting point of the third transverse direction distance 130 can be a position 132 on the longitudinal direction plane 120 located at a distance from the first waist edge 22 which is five-eighths of the absorbent article length 70. The third transverse direction distance 130 can be less than 70% or 65% of the first transverse direction distance 122.

The absorbent article 10 can include a chassis 100 and an absorbent assembly 50 bonded to the chassis 100. The chassis 100 can extend from the front waist edge 22 of the front region 20, through the crotch region 40, and to the back waist edge 32 of the back region 30. In various embodiments, the chassis 100 can be formed from multiple layers of material and can have a garment facing layer 102 providing a garment facing surface 104 and an absorbent assembly facing layer 106 providing an absorbent assembly facing surface 108. The absorbent assembly 50 can be bonded to the absorbent assembly facing surface 108 of the absorbent assembly facing layer 106 in any manner deemed suitable such as, for example, utilizing adhesive, ultrasonic bonding, thermal bonding, pressure bonding, etc.

In various embodiments, the material forming each of the garment facing layer 102 of the chassis 100 and the absorbent assembly facing layer 106 of the chassis 100 can be the same material. In various embodiments, the material forming each of the garment facing layer 102 of the chassis 100 and the absorbent assembly facing layer 106 of the chassis 100 can be different. In various embodiments, the material forming the garment facing layer 102 of the chassis 100 and/or the absorbent assembly facing layer 106 of the chassis 100 can be liquid permeable. In various embodiments, the material forming the garment facing layer 102 of the chassis 100 and/or the absorbent assembly facing layer 106 of the chassis 100 can be liquid impermeable. In various embodiments, the material forming the garment facing layer 102 of the chassis 100 and/or the absorbent assembly facing layer 106 of the chassis 100 can be vapor permeable. In various embodiments, the material forming the garment facing layer 102 of the chassis 100 and/or the absorbent assembly facing layer 106 of the chassis 100 can be vapor impermeable.

In various embodiments, the garment facing layer 102 of the chassis 100 and/or the absorbent assembly facing layer 106 of the chassis 100 can be formed from any suitable fibrous nonwoven web. For example, in various embodiments, the garment facing layer 102 of the chassis 100 and/or the absorbent assembly facing layer 106 of the chassis 100 can be formed from nonwoven webs such as staple fibers webs or more continuous fiber or filament fibers webs such as are found in meltblown or spunbond webs.

Through air bonded carded staple fibers webs may also be suitable for the garment facing layer 102 of the chassis 100 and/or the absorbent assembly facing layer 106 of the chassis 100 as fibers such as bicomponent fibers can be used which can include polyethylene-based polymers for the sheaths to provide a softer feel and hand, while the cores of the bicomponent fibers can be made from such polymers as polypropylene and polyester to provide other properties such as rigidity and compression resilience. In various embodiments, the garment facing layer 102 of the chassis 100 and/or the absorbent assembly facing layer 106 of the chassis 100 can be made from spunbond webs or combinations of spunbond and meltblown webs which are typically made from polypropylene-based polymers. In various embodiments, the basis weight of each of the garment facing layer 102 of the chassis 100 and the absorbent assembly facing layer 106 of the chassis 100 can be from about 10 or 15 gsm to about 35, 50, or 100 gsm.

The front region 20 of the absorbent article 10 and the back region 30 of the absorbent article 10 can include an elastic material such that, upon application of a stretching force, they are stretchable in the transverse direction (Y) and which, upon release of the stretching force, they contract/return at least a portion of their stretched length, to their original dimension. The elastic material within each of the front region 20 and the back region 30 can be sandwiched between the garment facing layer 102 of the chassis 100 and the absorbent assembly facing layer 106 of the chassis 100. The elastic materials can be sandwiched and held between the garment facing layer 102 of the chassis 100 and the absorbent assembly facing layer 106 of the chassis 100 with adhesive, ultrasonic bonding, heat pressure sealing, or any other means deemed suitable. The elastic material within the front region 20 can extend continuously between the first longitudinal direction side edge 24 and the second longitudinal direction side edge 26 of the front region 20. The elastic material within the back region 30 can extend continuously between the first longitudinal direction side edge 34 and the second longitudinal direction side edge 36 of the back region 30. Continuous extension of the elastic material in the transverse direction (Y) in each of the front region 20 and the back region 30 can provide for continuous tension of the elastic material in the transverse direction (Y) in the front region 20 and the back region 30. In other words, the elastic material in each of the front region 20 and the back region 30 remains active and capable of stretching/retracting continuously in the transverse direction (Y) throughout the length of the elastic material in the transverse direction (Y) of the absorbent article 10. In various embodiments, it may be deemed suitable to inactivate a portion of the elastic material in the front region 20 and/or back region 30. Inactivation of the elastic material can be accomplished via any method deemed suitable such as, for example, cutting the elastic material, thermally pressing the elastic material, or any other suitable method.

Figure 5:
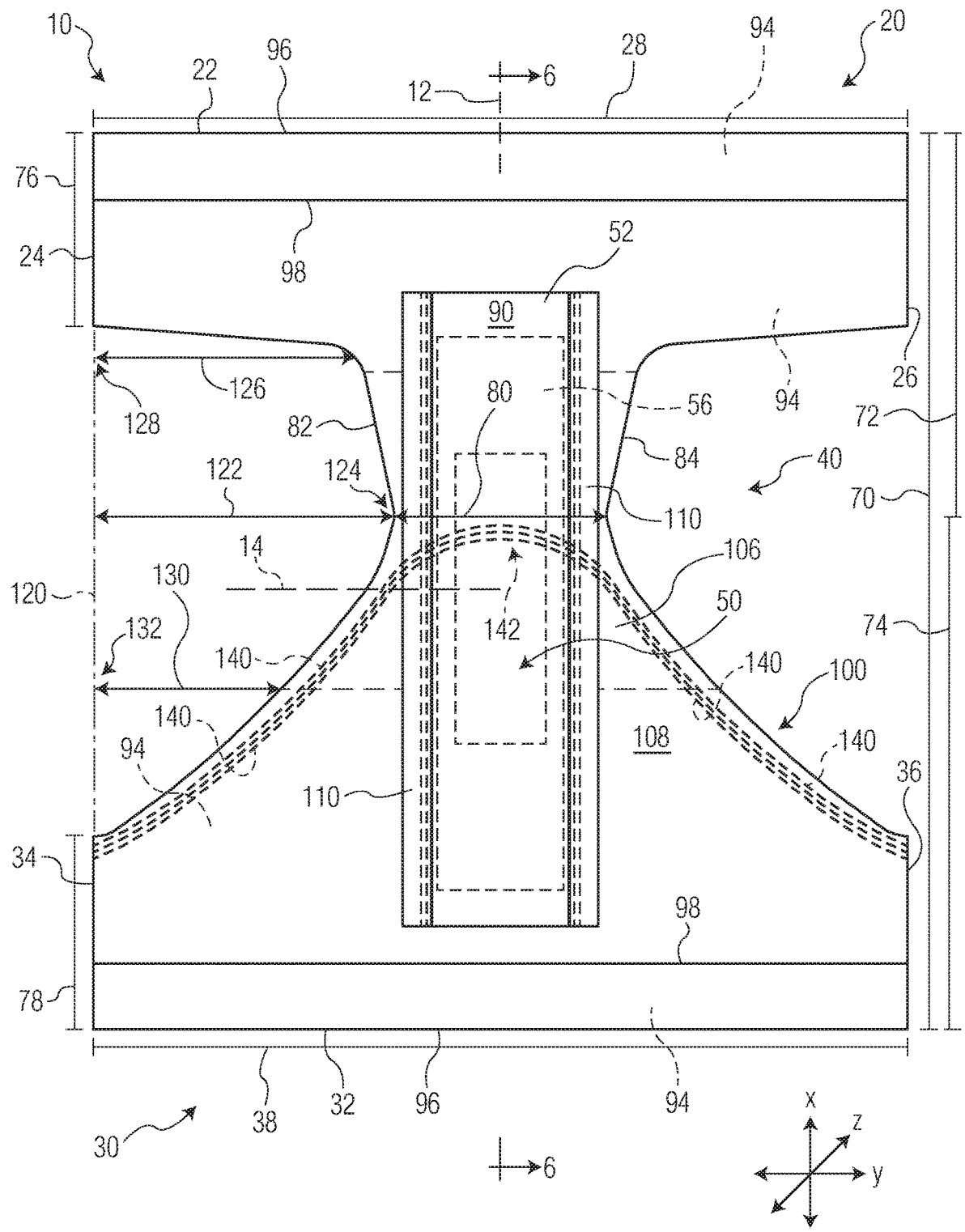
FIG. 5 is an illustration of a plan view of an alternate embodiment of an absorbent article in a first configuration which is a longitudinally and transverse stretched and laid-flat configuration with the surface of the absorbent article that faces the wearer when the absorbent article is worn facing the viewer.

In various embodiments, in addition to elastic material extending in the transverse direction (Y) between each of the first longitudinal direction side edge 24 and second longitudinal direction side edge 26 of the front region 20 and between the first longitudinal direction side edge 34 and the second longitudinal direction side edge 36 of the back region 30, elastic material can also extend in the transverse direction (Y) between the first non-linear leg edge 82 and the second non-linear leg edge 84, such as, for example, illustrated in FIG. 1 and FIG. 5. In various embodiments, it may be deemed suitable to inactivate a portion of the elastic material extending between the first non-linear leg edge 82 and the second non-linear leg edge 84. Inactivation of the elastic material can be accomplished via any method deemed suitable such as, for example, cutting the elastic material, thermally pressing the elastic material, or any other suitable method. Providing elastic material in each of the front region 20 and back region 30 that extends in the transverse direction (Y) between their respective longitudinal direction side edges, 24, 26, 34, and 36, can provide tension to the absorbent article 10 about the waist of the wearer of the absorbent article 10 and can help maintain the absorbent article 10 about the torso of the wearer of the absorbent article 10. Providing elastic material that extends in the transverse direction (Y) between the first non-linear leg edge 82 and the second non-linear leg edge 84 can further provide support to the absorbent article 10 and can help maintain the absorbent assembly 50 in closer proximity to the body of the wearer of the absorbent article 10, thereby minimizing leakage of body exudates from the absorbent article 10 and improving comfort to the wearer of the absorbent article 10. In various embodiments, within the back region 30 and the crotch region 40 of the absorbent article 10, the elastic material can extend in the transverse direction (Y) between the first longitudinal direction side edge 34 and the second longitudinal direction side edge 36 as well as between the first non-linear leg edge 82 and the second non-linear leg edge 84 for a longitudinal length of the absorbent article 10 of three-eighths of the total absorbent article length 70 as measured from the back waist edge 32 of the absorbent article 10.

Figure 6:
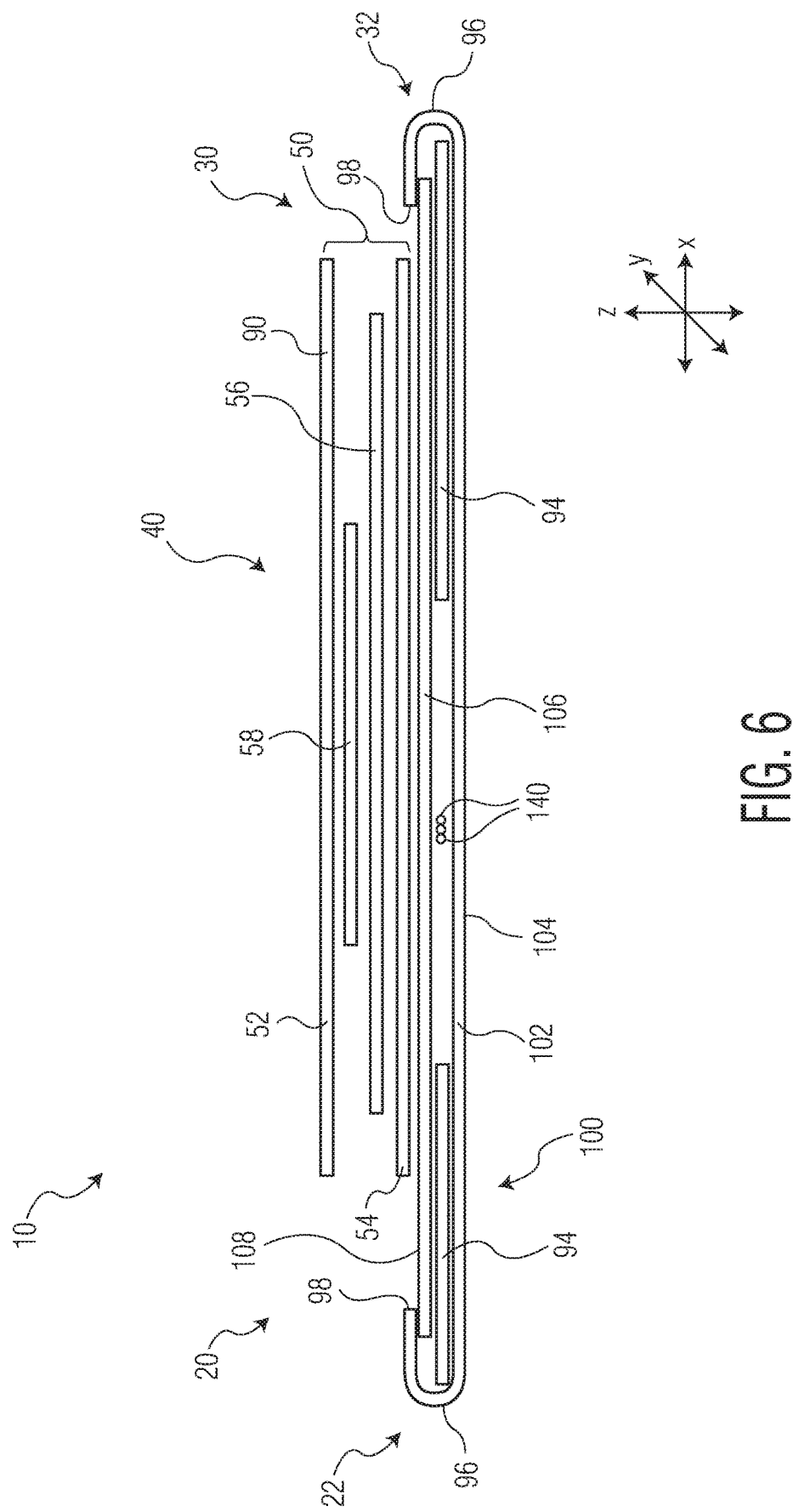
FIG. 6 is an illustration of a cross-sectional view of an embodiment of the absorbent article of FIG. 5 taken along line 6-6.

In various embodiments, such as, for example, illustrated in FIGS. 1 and 2, the elastic material in the absorbent article 10 can be elastomeric strands 92 of material such as can be preformed from LYCRA brand fibers/yarns for example. LYCRA is a registered trademark of E.I. DuPont DeNemours Co., Wilmington, DE, U.S.A. The elastomeric strands 92 can have a round, semi-circular, square, rectangular, oval, or other geometrical configuration. In various embodiments, such as, for example, illustrated in FIGS. 5 and 6, the elastic material in the absorbent article 10 can be an elastomeric polymeric film layer 94. In various embodiments, a suitable elastomeric polymeric film layer 94 can be a stretch-bonded laminate (SBL) in which an elastic core or middle layer is elongated before two opposing outer nonwoven web layers are bonded thereto. Another suitable material for the elastomeric polymeric film layer 94 is a necked bonded laminate (NBL). The NBL material is a three layer laminate but the elastic core or middle layer is not pre-stretched prior to being attached to the two outer nonwoven web layers. Instead, the opposing outer nonwoven web layers are necked stretched before the elastic core or middle layer is bonded to them. Other examples of such elastomeric materials that can be used as an elastomeric polymeric film layer 94 include a continuous filament stretch bonded laminate (CFSBL), a vertical filament laminate (VFL), a necked stretch bonded laminate (NSBL), or a necked thermal laminate (NTL). Combinations of such materials can also be used. Such materials are described in U.S. Pat. No. 4,720,415 to Vander Wielen et al., U.S. Pat. No. 5,366,793 to Fitts, et al., U.S. Pat. No. 5,385,775, to Wright, U.S. Pat. No. 6,969,441 to Welch et al., U.S. Pat. No. 6,978,486 to Zhou et al., U.S. Pat. No. 7,803,244 to Siqueira et al., and U.S. Pat. No. 5,226,992 to Morman et al., each of which are hereby incorporated by reference thereto in its entirety. The elastomeric laminates just described will typically include an elastomeric layer and at least one surface-bonded nonwoven web layer such as a meltblown, spunbond, or through-air bonded web.

Each of the front region 20 and the back region 30 can have a portion which can be the waist portion of the absorbent article 10. In various embodiments, the waist portion of each of the front region 20 and the back region 30 can have a length in the longitudinal direction (X) which is less than about 5, 4, or 3% of the absorbent article length 70. In various embodiments, the waist portion of each of the front region 20 and back region 30 can be formed by folding over a portion of the garment facing layer 102 of the chassis 100 onto itself and creating a folded edge 96 at each of the front waist edge 22 and back waist edge 32. The folding over of a portion of the garment facing layer 102 of the chassis 100 can also encase a portion of the elastic material within the front region 20 and back region 30 into the waist portion of each of the front region 20 and back region 30. In the illustrative and exemplary embodiments of FIGS. 1 and 2, the waist portions of each of the front region 20 and the back region 30 can be illustrated as the portion wherein the elastic lycra strands 92 are sandwiched between the garment facing layer 102 of the chassis 100 which has been folded over onto itself creating a folded edge 96 and placing a material edge 98 on the interior of the absorbent article 10. Similarly, in the exemplary embodiments illustrated in FIGS. 5 and 6, the waist portions of each of the front region 20 and the back region 30 can be illustrated as the portion wherein the elastomeric polymeric film layer 94 are sandwiched between the garment facing layer 102 of the chassis 100 which has been folded over onto itself creating a folded edge 96 and placing a material edge 98 on the interior of the absorbent article 10.

The absorbent article 10 can also include an absorbent assembly 50. The absorbent assembly 50 can extend in the longitudinal direction (X) of the absorbent article 10 from the front region 20, through the crotch region 40, and to the back region 30. In various embodiments, the absorbent assembly 50 can have at least a topsheet layer 52, a backsheet layer 54, and an absorbent core 56 positioned between the topsheet layer 52 and the backsheet layer 54. In various embodiments, the absorbent assembly 50 can have at least a topsheet layer 52, a backsheet layer 54, an absorbent core 56 positioned between the topsheet layer 52 and the backsheet layer 54, and a surge layer 58 positioned between the absorbent core 56 and the topsheet layer 52. The topsheet layer 52 can be bonded to the backsheet layer 54 beyond the outermost edge of the absorbent core 56 to form a perimeter seal for the absorbent assembly 50. The perimeter seal can contain the body exudates within the absorbent assembly 50 of the absorbent article 10.

The topsheet layer 52 defines a body facing surface 90 of the absorbent assembly 50 that may directly contact the body of the wearer and is liquid permeable to receive body exudates. The topsheet layer 52 is desirably provided for comfort and functions to direct body exudates away from the body of the wearer, through its own structure, and towards the absorbent core 56. The topsheet layer 52 desirably retains little to no liquid in its structure, so that it provides a relatively comfortable and non-irritating surface next to the skin of the wearer of the absorbent article 10.

The topsheet layer 52 can be a single layer of material, or alternatively, can be multiple layers that have been laminated together. The topsheet layer 52 can be constructed of any material such as one or more woven sheets, one or more fibrous nonwoven sheets, one or more aperture film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 52.

In various embodiments the topsheet layer 52 can be constructed from various nonwoven webs such as meltblown webs, spunbond webs, hydroentangled spunlace webs, or through air bonded carded webs. Examples of suitable topsheet layer 52 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 52 can be a bonded carded web made of polypropylene and polyethylene such as that obtainable from Sandler Corp., Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 52, each of which is hereby incorporated by reference thereto in its entirety. Additional topsheet layer 52 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the topsheet layer 52 may contain a plurality of apertures formed therethrough to permit body exudates to pass more readily into the absorbent core 56. The apertures may be randomly or uniformly arranged throughout the topsheet layer 52. The size, shape, diameter, and number of apertures may be varied to suit an absorbent article's 10 particular needs.

In various embodiments, the tospheet layer 52 can have a basis weight ranging from about 5, 10, 15, 20, or 25 gsm to about 50, 100, 120, 125, or 150 gsm. For example, in an embodiment, a topsheet layer 52 can be constructed from a through air bonded carded web having a basis weight ranging from about 15 gsm to about 100 gsm. In another example, a topsheet layer 52 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics, and others.

In various embodiments, the topsheet layer 52 can be at least partially hydrophilic. In various embodiments, a portion of the topsheet layer 52 can be hydrophilic and a portion of the topsheet layer 52 can be hydrophobic. In various embodiments, the portions of the topsheet layer 52 which can be hydrophobic can be either an inherently hydrophobic material or can be a material treated with a hydrophobic coating.

In various embodiments, the topsheet layer 52 can be a multicomponent topsheet layer 52 such as by having two or more different nonwoven or film materials, with the different materials placed in separate locations in the transverse direction (Y) of the absorbent assembly 50. For example, the topsheet layer 52 can be a two layer or multicomponent material having a central portion positioned along and straddling a longitudinal axis 12 of an absorbent article 10, with lateral side portions flanking and bonded to each side edge of the central portion. The central portion can be constructed from a first material and the side portions can be constructed from a material which can be the same as or different from the material of the central portion. In such embodiments, the central portion may be at least partially hydrophilic and the side portions may be inherently hydrophobic or may be treated with a hydrophobic coating. Examples of constructions of multi-component topsheet layers are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

In various embodiments, a central portion of a topsheet layer 52 can be positioned symmetrically about the absorbent article 10 longitudinal axis 12. Such central longitudinally directed central portion can be a through air bonded carded web ("TABCW") having a basis weight between about 15 and about 100 gsm. Previously described nonwoven, woven, and aperture film topsheet layer materials may also be used as the central portion of a topsheet layer 52. In various embodiments, the central portion can be constructed from a TABCW material having a basis weight from about 20 gsm to about 50 gsm such as is available from Xiamen Yanjan Industry, Beijing, DaYuan Nonwoven Fabrics, and others. Alternatively, aperture films, such as those available from such film suppliers as Texol, Italy and Tredegar, U.S.A. may be utilized. Different nonwoven, woven, or film sheet materials may be utilized as the side portions of the topsheet layer 52. The selection of such topsheet layer 52 materials can vary based upon the overall desired attributes of the topsheet layer 52. For example, it may be desired to have a hydrophilic material in the central portion and hydrophobic-barrier type materials in the side portions to prevent leakage and increase a sense of dryness in the area of the side portions. Such side portions can be adhesively, thermally, ultrasonically, or otherwise bonded to the central portion along or adjacent the longitudinally directed side edges of the central portion. Traditional absorbent article construction adhesive may be used to bond the side portions to the central portion. Either of the central portion and/or the side portions may be treated with surfactants and/or skin-health benefit agents, as are well known in the art.

Such longitudinally directed side portions can be of a single or multi-layered construction. In various embodiments, the side portions can be adhesively or otherwise bonded laminates. In various embodiments, the side portions can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as polyethylene having a basis weight from about 10 to about 40 gsm. Construction adhesive can be utilized to laminate the spunbond layer to the film layer at an add-on level of between about 0.1 gsm and 15 gsm. When a film barrier layer is used in the overall topsheet layer 52 design, it may include opacifying agents, such as film pigments, that can help the film in masking stains along the absorbent article 10 side edges, thereby serving as a masking element. In such a fashion, the film layer can serve to limit visualization of a fluid insult stain along the absorbent assembly 50 side edges when viewed from above the topsheet layer 52. The film layer may also serve as a barrier layer to prevent rewet of the topsheet layer 52 as well as to prevent the flow of fluid off the side edges of the absorbent assembly 50. In various embodiments, the side portions can be laminates such as a spunbond-melt-blown-meltblown-spunbond layer ("SMMS") laminate, spunbond-film laminate, or alternatively, other nonwoven laminate combinations.

The backsheet layer 54 of the absorbent assembly 50 is generally liquid impermeable and is the portion of the absorbent assembly 50 which faces the garments of the wearer. The backsheet layer 54 can permit the passage of air or vapor out of the absorbent article 10 while still blocking the passage of liquids. Any liquid impermeable material may generally be utilized to form the backsheet layer 54. The backsheet layer 54 can be composed of a single layer or multiple layers, and these one or more layers can themselves comprise similar or different materials. Suitable material that may be utilized can be a microporous polymeric film, such as a polyolefin film or polyethylene or polypropylene, nonwovens, and nonwoven laminates, and film/nonwoven laminates. The particular structure and composition of the backsheet layer 54 can be selected from various known films and/or fabrics with the particular material being selected as appropriate to provide the desired level of liquid barrier, strength, abrasion resistance, tactile properties, aesthetics, and so forth. In various embodiments, a polyethylene film can be utilized that can have a thickness in the range of from about 0.2 or 0.5 mils to about 3.0 or 5.0 mils. An example of a backsheet layer 54 can be a polyethylene film such as that obtainable from Pliant Corp., Schaumburg, IL, USA. Another example can include calcium carbonate-filled polypropylene film. In still another embodiment, the backsheet layer 54 can be a hydrophobic nonwoven material with water barrier properties such as a nonwoven laminate, an example of which can be a spunbond, meltblown, meltblown, spunbons, four-layered laminate.

In various embodiments, the backsheet layer 54 can be a two layer construction, including an outer layer material and an inner layer material which can be bonded together. The outer layer can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer can be a 20 gsm spunbond polypropylene non-woven web. The inner layer can be either vapor permeable (i.e., "breathable") or vapor impermeable. The inner layer may be manufactured from a thin plastic film, although other liquid impermeable materials may also be used. The inner layer can inhibit liquid body exudates from leaking out of the absorbent assembly 50 and wetting articles, such as bed sheets and clothing, as well as the wearer and caregiver. An example of a material for an inner layer can be a printed 19 gsm Berry Plastics XP-8695H film or equivalent commercially available from Berry Plastics Corporation, Evansville, IN, U.S.A.

The backsheet layer 54 can, therefore, be of a single or multiple layer construction, such as of multiple film layers or laminates of film and nonwoven fibrous layers. Suitable backsheet layers 54 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

An absorbent core 56 can be positioned between the topsheet layer 52 and the backsheet layer 54 of the absorbent article 10. In various embodiments, the absorbent core 56 can extend in the longitudinal direction (X) of the absorbent assembly 50. The absorbent core 56 can have a first portion located in the crotch region 40 of the absorbent article 10. In various embodiments, the absorbent core 56 can have a second portion located in a portion of at least one of the front region 20 or the back region 30. In various embodiments, the absorbent core 56 can have a first portion located within the crotch region 40 and a second portion located in a portion of the front region 20. In various embodiments, the absorbent core 56 can have a first portion located within the crotch region 40 and a second portion located in a portion of the back region 30. In various embodiments, an absorbent core 56 can have a first portion located within the crotch region 40, a second portion located in a portion of the front region 20, and a third portion located in a portion of the back region 30.

The absorbent core 56 can generally be any single layer structure or combination of layer components, which can demonstrate some level of compressibility, conformability, be non-irritating to the wearer's skin, and capable of absorbing and retaining liquids and other body exudates. In various embodiments, the absorbent core 56 can be formed from a variety of different materials and can contain any number of desired layers. For example, the absorbent core 56 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of wood pulp fluff can be identified with the trade designation NB416, available from Weyerhaeuser Corp., and is a bleached, highly absorbent wood pulp containing primarily soft wood fibers.

In various embodiments, if desired, the absorbent core 56 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 56 in any amount as desired.

Regardless of the combination of absorbent materials used in the absorbent core 56, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The shape of the absorbent core 56 can vary as desired and can comprise any one of various shapes including, but not limited to, triangular, rectangular, dog-bone, and elliptical shapes. In various embodiments, the absorbent core 56 can have a shape that generally corresponds with the overall shape of the absorbent assembly 50. The dimensions of the absorbent core 56 can be substantially similar to those of the absorbent assembly 50, however, it will be appreciated that the dimensions of the absorbent core 56 while similar, will often be less than those of the overall absorbent assembly 50, in order to be adequately contained therein.

By way of example, suitable materials and/or structures for the absorbent core 56 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al. each of which is hereby incorporated by reference thereto in its entirety.

In various embodiments, an absorbent core 56 can be a single layer structure and can include, for example, a matrix of cellulosic fluff and superabsorbent material. In various embodiments, an absorbent core 56 can have at least two layers of material, such as, for example, a body facing layer and a garment facing layer. In various embodiments, the two layers can be identical to each other. In various embodiments, the two layers can be different from each other. In such embodiments, the two layers can provide the absorbent article 10 with different absorption properties as deemed suitable. In various embodiments, the body facing layer of the absorbent core 56 may be constructed of an airlaid material and the garment facing layer of the absorbent core 56 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

In various embodiments, the absorbent assembly 50 can include a surge layer 58 positioned between the absorbent core 56 and the topsheet layer 52. The surge layer 58 can be adapted to work with the absorbent core 56 in absorbing body exudates. In various embodiments, the surge layer 58 can have a higher void volume that the absorbent core 56 to quickly intake and hold body exudates so that the absorbent core 56 has time to absorb the body exudates without such body exudates leaking from the absorbent article 10. The surge layer 58 can take on any size and shape as desired and as deemed suitable. For example, in FIG. 1, the surge layer 58 is illustrated in the shape of a rectangle and has a size dimension smaller than the absorbent core 56.

The absorbent assembly 50 can be configured to contain body exudates discharged from the wearer of the absorbent article 10. For example, containment flaps 110 are configured to provide a barrier to the transverse direction (Y) flow of body exudates. A flap elastic member 112 can be operatively joined with each containment flap 110. The elasticized containment flaps 110 can have a partially unattached free edge 114 which can assume an upright configuration in at least the crotch region 40 of the absorbent article 10 to form a seal against the wearer's body during use. In various embodiments, the containment flaps 110 can extend in the longitudinal direction (X) along the entire length of the absorbent assembly 50 or may only extend partially along the length of the absorbent assembly 50.

In various embodiments, the containment flaps 110 can be constructed of a fibrous material which can be similar to the material forming the topsheet layer 52. In various embodiments, exemplary material to form the containment flaps 110 can include polyolefinic films, microporous or other breathable formed films, breathable monolithic films, and hydrophobic nonwovens. Examples of hydrophobic nonwovens can include spunbond meltblown, spunbond-meltblown-spunbond, and spunbond-meltblown-meltblown-spunbond composites. Other conventional materials including multiple layers of film and/or nonwovens can be used to form the containment flap material.

In various embodiments, the containment flaps 110 can be integrally formed with the absorbent assembly 50 and can be extensions of the material forming the topsheet layer 52 and/or the backsheet layer 54. In various embodiments, such as, for example, illustrated in FIGS. 3 and 4, the containment flaps 110 can be formed separately from the absorbent assembly 50 and can be bonded to the absorbent assembly 50 and/or the chassis 100 of the absorbent article 10. In such embodiments wherein each containment flap 110 is formed separate from the absorbent assembly 50, the material forming each containment flap 110 can have a pair of longitudinally extending edges, 116 and 118. In various embodiments, each of the containment flaps 110 can be configured such that a portion of the containment flaps 110 is positioned between the garment facing surface of the backsheet layer 54 of the absorbent assembly 50 and the absorbent assembly facing surface 108 of the absorbent assembly facing layer 106 of the chassis 100. In such a configuration, the longitudinally extending edge 118 of the material forming the containment flaps 110 can be positioned between the garment facing surface of the backsheet layer 54 of the absorbent assembly 50 and the absorbent assembly facing surface 108 of the absorbent assembly facing layer 106 of the chassis 100. At least a portion of the material forming the containment flaps 110 can be folded over onto itself to encase the flap elastic member(s) 112 which are operatively associated with the containment flaps 110. The portion of the containment flaps 110 containing the folded over material can form the at least partially unattached free edge 114 of each of the containment flaps 110 which can extend in the longitudinal direction of the absorbent assembly 50 and can be positioned to be in an overlapping configuration with the topsheet layer 52 of the absorbent assembly 50. In various embodiments, the encased flap elastic member(s) 112 can be located in proximity to the at least partially unattached free edge 114 of each of the containment flaps 110. In various embodiments such as, for example, illustrated in FIG. 3, the longitudinally extending edge 116 of the material forming the containment flaps 110 can be positioned above the topsheet layer 52 of the absorbent assembly 50. In various embodiments such as, for example, illustrated in FIG. 4, the longitudinally extending edge 116 of each of the containment flaps 110 can be positioned adjacent the garment facing surface of the backsheet layer 54 of the absorbent assembly 50. In such embodiments, each of the longitudinally extending edges, 116 and 118, of the containment flaps 110 can be positioned between the garment facing surface of the backsheet layer 54 of the absorbent assembly 50 and the absorbent assembly facing surface 108 of the absorbent assembly facing layer 106 of the chassis 100.

In various embodiments, the absorbent article 10 can further have a leg elastic 140. In various embodiments, the absorbent article 10 can have 1, 2, 3, 4, or 5 leg elastics 140. The leg elastic 140 can be positioned between the garment facing layer 102 and the absorbent assembly facing layer 106 of the chassis 100. Each leg elastic 140 can be a single strand, ribbon, or strip of elastomeric material. For example, the absorbent article 10 illustrated in FIG. 1 illustrates three strands of leg elastics 140. In various embodiments, a leg elastic 140 can be positioned in the front region 20 of the absorbent article 10. In various embodiments, a leg elastic 140 can be positioned in the back region 30 of the absorbent article 10. In various embodiments, a leg elastic 140 can extend into the crotch region 40 of an absorbent article 10 from either the front region 20 or the back region 30. For example, in various embodiments, such as illustrated in FIG. 1, the leg elastic 140 can extend from the first longitudinal direction side edge 34 of the back region 30 to the second longitudinal direction side edge 36 of the back region 30. The leg elastic 140 can be non-linear as it extends from the first longitudinal direction side edge 34 of the back region to the second longitudinal direction side edge 36 of the back region 30. In the non-linear configuration, the leg elastic 140 can initiate at the first longitudinal direction side edge 34 of the back region 30, follow the contour of the first non-linear side edge 82, overlap with the absorbent assembly 50, follow the contour of the second non-linear side edge 84, and terminate at the second longitudinal direction side edge 36 of the back region 30. In the non-linear configuration, the leg elastic 140 can have an apex 142 positioned between the absorbent article narrowest width 80 and the transverse axis 14 of the absorbent article 10 in the crotch region 40 of the absorbent article 10. The apex 142 of the leg elastic 140 can be in an overlapping configuration with the absorbent assembly 50. Providing a leg elastic 140 which has an apex 142 between the absorbent article narrowest width 80 and the transverse axis 14 can provide tension to the absorbent article 10 in the crotch region 40 of the absorbent article 10 and maintain the absorbent assembly 50 of the absorbent article 10 in closer contact with the wearer of the absorbent article 10. Such closer contact between the absorbent assembly 50 and the body of the wearer of the absorbent article 10 can reduce or prevent leakage of body exudate from the absorbent article 10.

In various embodiments, it may be deemed suitable to alter the tension provided by the leg elastic 140 in order to reduce the amount of tension provided by the leg elastic 140. A reduction in the tension provided by the leg elastic 140 may be deemed suitable as the combination of the tension provided by the elastic material 92 and the leg elastic 140 may result in bunching of the absorbent article 10 and protrusion of the absorbent article away from the body of the wearer of the absorbent article 10. In various embodiments, the tension provided by leg elastic(s) 140 may be altered by selectively deadening the leg elastic 140 such that the leg elastic 140 is no longer capable of exhibiting the ability to stretch and retract along its entire length. In various embodiments, selective deadening can occur via cutting the leg elastic 140 or mechanically altering the leg elastic 140. In various embodiments in which more than one leg elastic 140 is provided, each leg elastic 140 may have a tension different from the other leg elastic 140 such as, for example, a different decitex or a different elongation stress during formation.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any documents is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. An absorbent article comprising:
   a. a longitudinal direction and a transverse direction;
   b. a longitudinal axis and a transverse axis;
   c. a front region comprising a first waist edge, a first longitudinal direction side edge, a second longitudinal direction side edge transversely opposed to the first longitudinal direction side edge, the front region comprising an elasticated material extending from the first longitudinal direction side edge to the second longitudinal direction side edge;
   d. a back region comprising a second waist edge, a third longitudinal direction side edge, a fourth longitudinal direction side edge transversely opposed to the third longitudinal direction side edge, the back region comprising an elasticated material extending from the third longitudinal direction side edge to the fourth longitudinal direction side edge;
   e. a crotch region located between the front region and the back region and comprising an absorbent article narrowest width in the transverse direction wherein the absorbent article narrowest width is located between the transverse axis and the first waist edge;
   f. an absorbent article length measured from the first waist edge to the second waist edge;
   g. a first non-linear leg edge extending between and connecting the first longitudinal direction side edge of the front region to the third longitudinal direction side edge of the back region;
   h. a second non-linear leg edge extending between and connecting the second longitudinal direction side edge of the front region to the fourth longitudinal direction side edge of the back region;
   i. a first configuration wherein, in an unfolded and laid-flat configuration, the first longitudinal direction side edge of the front region is aligned with the third longitudinal direction side edge of the back region and a first longitudinal direction plane is formed between the first longitudinal direction side edge and the third longitudinal direction side edge;
   j. a first transverse direction distance measured from a first position on the first longitudinal direction plane to a first position on the first non-linear leg edge located at the absorbent article narrowest width;
   k. a second transverse direction distance measured from a second position on the first longitudinal direction plane located at one-quarter of the absorbent article length from the first waist edge to a second position on the first non-linear leg edge wherein the second transverse direction distance is greater than 75% of the first transverse direction distance;
   l. a first non-linear leg elastic extending from the third longitudinal direction side edge of the back region to the fourth longitudinal direction side edge of the back region and having an apex positioned between the absorbent article narrowest width and the transverse axis; and
   m. a second configuration wherein the article has a first side seam connecting the first longitudinal direction side edge of the front region to the third longitudinal direction side edge of the back region and a second side seam connecting the second longitudinal direction side edge of the front region to the fourth longitudinal direction side edge of the back region, the first side seam and the second side seam being formed by permanent bonds.

2. The absorbent article of claim 1 comprising a third transverse direction distance measured from a third position on the first longitudinal direction plane located at five-eighths of the absorbent article length from the first waist edge to a third position on the first non-linear edge wherein the third transverse direction distance is less than 70% of the first transverse direction distance.

3. The absorbent article of claim 1 wherein a tangent line to the first non-linear leg edge is not parallel to the transverse axis of the absorbent article along the entire length of the first non-linear leg edge.

4. The absorbent article of claim 1 wherein the second transverse direction distance is greater than 80% of the first transverse direction distance.

5. The absorbent article of claim 2 wherein the third transverse direction distance is less than 65% of the first transverse direction distance.

6. The absorbent article of claim 1 further comprising a chassis wherein the chassis comprises a first nonwoven layer and a second nonwoven layer.

7. The absorbent article of claim 6 wherein the first nonwoven layer of the chassis and the second nonwoven layer of the chassis extend continuously from the first waist edge of the absorbent article to the second waist edge of the absorbent article.

8. The absorbent article of claim 6 comprising a first elastic material sandwiched between the first nonwoven layer and the second nonwoven layer in the front region and extending in the transverse direction from the first longitudinal direction side edge to the second longitudinal direction side edge in the front region and a second elastic material sandwiched between the first nonwoven layer and the second nonwoven layer in the back region and extending in the transverse direction from the third longitudinal direction side edge to the fourth longitudinal direction side edge in the back region.

9. The absorbent article of claim 8 wherein the first elastic material and the second elastic material is a plurality of elastomeric strands.

10. The absorbent article of claim 8 wherein the first elastic material and the second elastic material is an elastomeric polymeric film layer.

11. The absorbent article of claim 6 further comprising an absorbent assembly bonded to the first nonwoven layer of the chassis, the absorbent assembly comprising a topsheet layer, a backsheet layer, and an absorbent core positioned between the topsheet layer and the backsheet layer.

12. The absorbent article of claim 11 wherein the absorbent assembly comprises a first longitudinally extending containment flap and a second longitudinally extending containment flap transversely opposed to the first longitudinally extending containment flap.

13. The absorbent article of claim 12 wherein each of the first longitudinally extending containment flap and the second longitudinally extending containment flap comprise a portion positioned between the backsheet layer of the absorbent assembly and the first nonwoven layer of the chassis.

14. The absorbent article of claim 1 wherein each of the first longitudinal direction side edge and the second longitudinal direction side edge have a longitudinal length less than 25% of the absorbent article length.

15. The absorbent article of claim 1 wherein each of the third longitudinal direction side edge and the fourth longitudinal direction side edge have a longitudinal length less than 25% of the absorbent article length.

16. The absorbent article of claim 1, wherein the first non-linear leg edge is concave along its entire length between the first longitudinal direction side edge of the front region and the third longitudinal direction side edge of the back region and wherein the second non-linear leg edge is concave along its entire length between the second longitudinal direction side edge of the front region and the fourth longitudinal direction side edge of the back region.

* * * * *